(12) United States Patent
Edwards

(10) Patent No.: US 7,393,995 B2
(45) Date of Patent: *Jul. 1, 2008

(54) NON-PUNGENT ORNAMENTAL PEPPERS

(76) Inventor: Marlin Edwards, 1445 Bald Eagle Rd., Wildwood, MO (US) 63038

( * ) Notice: Subject to any disclaimer, the term of this patent is extended or adjusted under 35 U.S.C. 154(b) by 0 days.

This patent is subject to a terminal disclaimer.

(21) Appl. No.: 11/247,632

(22) Filed: Oct. 11, 2005

(65) Prior Publication Data

US 2006/0085874 A1 Apr. 20, 2006

Related U.S. Application Data

(63) Continuation-in-part of application No. 09/564,153, filed on May 3, 2000, now Pat. No. 7,087,819.

(60) Provisional application No. 60/132,389, filed on May 4, 1999.

(51) Int. Cl.
*A01H 1/00* (2006.01)
(52) U.S. Cl. .................................. 800/266; 800/260
(58) Field of Classification Search .................. 800/260, 800/266, 317.1
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,811,640 A | 9/1998 | Grun et al. | |
| 5,850,009 A | 12/1998 | Kevern | |
| 5,959,186 A | 9/1999 | Arevalos et al. | |
| 7,087,819 B2 * | 8/2006 | Edwards | .............. 800/317.1 |

OTHER PUBLICATIONS

Harvell et al 1997, HortScience 32(7): 1292.*
Bosland, P.W. 1996. Capsicums: Innovative uses of an ancient crop. p. 479-487. In: J. Janick (ed.), Proress in new crops. ASHS Press, Arlington, VA.*
"Sweet Pickle" available from Park Seed 1991 p. 112.*
Cross Country Nurseries, www.chiliplants.com, "Sweet Pickle".*
Dave DeWitt, *The Chile Pepper Encyclopedia*, William Morrow and Company, Inc. p. 217-18 (1999).
Dave DeWitt & Paul W. Bosland, *Peppers of the World*, Ten Speed Press, p. 96, 102, 105, 106, 107, 108, 109, 110, 111, 113, 117 (1996).
Dave DeWitt and Nancy Gerlach, *The Whole Chile Pepper Book*, Little, Brown and Company, p. 30-31 (1990).
Miller et al., *American Society for Horticultural Science*, 544-550 (Date Unknown).
Eshbbaugh et al., *Bulletin of the Torrey Botanical Club* 102(6):396-403 (1976).
Deshapnde, *Indian Journal of Agricultural Science*, 5:513-516 (1935).
Cooper, et al., *J. Agric, Food Chem*. 39:2253-2256 (1991).
Lippert, et al., *The Botanical Review*, 32:24-55 (1966).
"Capsicum" *Hortus Third A Concise Dictionary of Plants Cultivated in the United States and Canada*, MacMillan Publishing Company 1976.
Harvell et al., "The Environment Produces a Significant Effect on Pungency of Chiles", 1997, HortScience, vol. 32, N. 7, p. 1292.
Barbara Pickersgill, Genetic Resources and Breeding of Capsicum Spp, 1997, *Euphytica*, vol. 96, pp. 129-133.
Jean Andrews, Peppers, The Domesticated Capsicums, 1984, Library of Congress, p. 83.
Thompson and Morgan Inc. Spring 1991 Catalog, P. O. Box 1308, Jackson, New Jersey 08527, p. 63.
PVP Variety Certificate 200000140 for Medusa filed Jan. 21, 2000.

* cited by examiner

*Primary Examiner*—David H Kruse
(74) *Attorney, Agent, or Firm*—Jondle & Associates, P.C.

(57) ABSTRACT

The present invention relates to new, distinct and stable *Capsicum annuum* plants that have an ornamental phenotype and produce fruit that is non-pungent.

10 Claims, 8 Drawing Sheets

96P601 PEDIGREE

96P631 PEDIGREE

97P1938 PEDIGREE

96P610 PEDIGREE

03P388-3 PEDIGREE

03P384-8 PEDIGREE

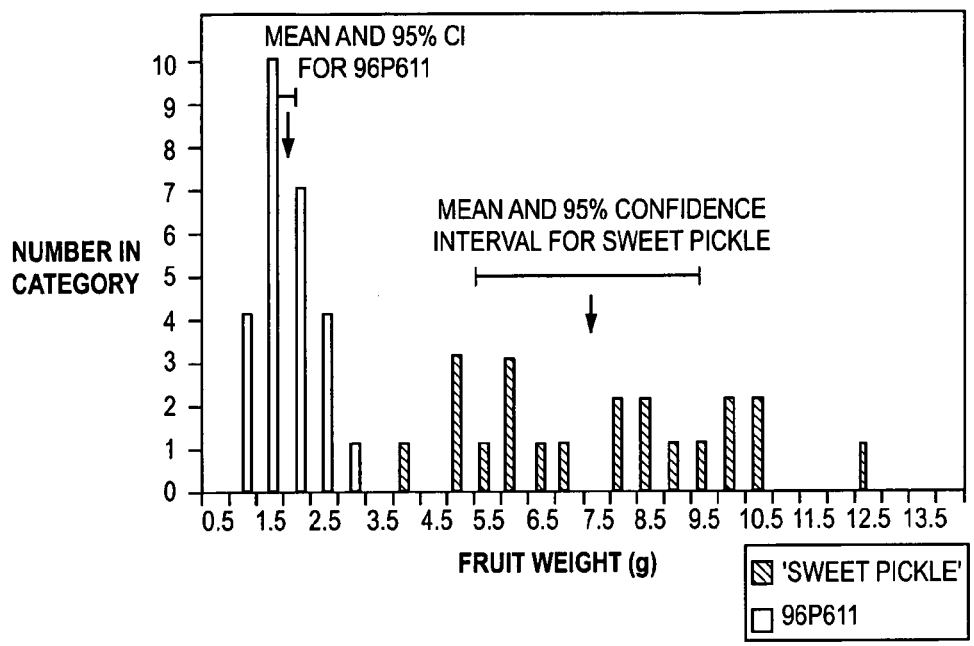
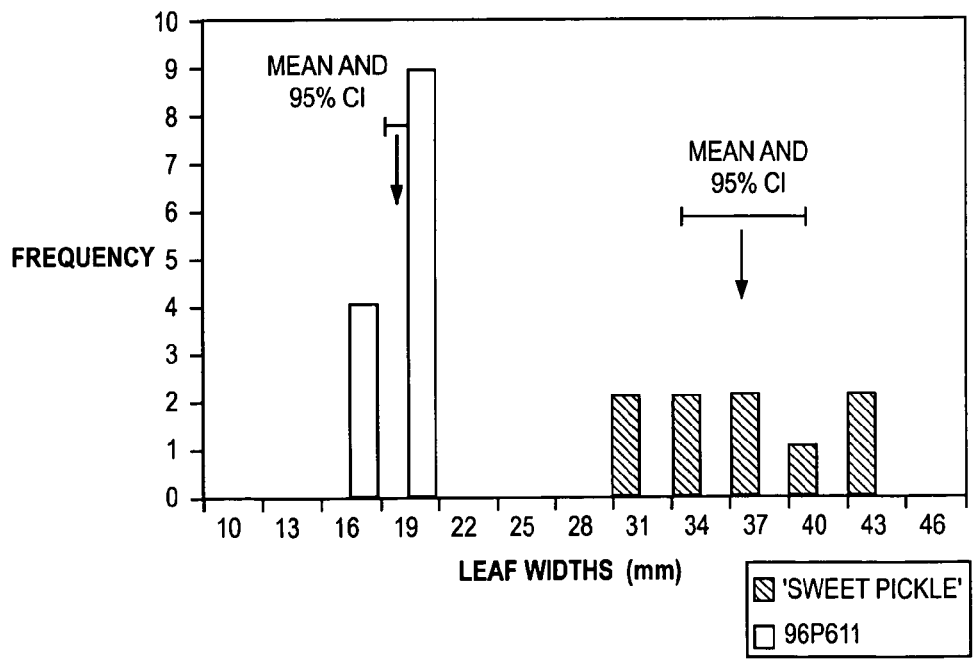

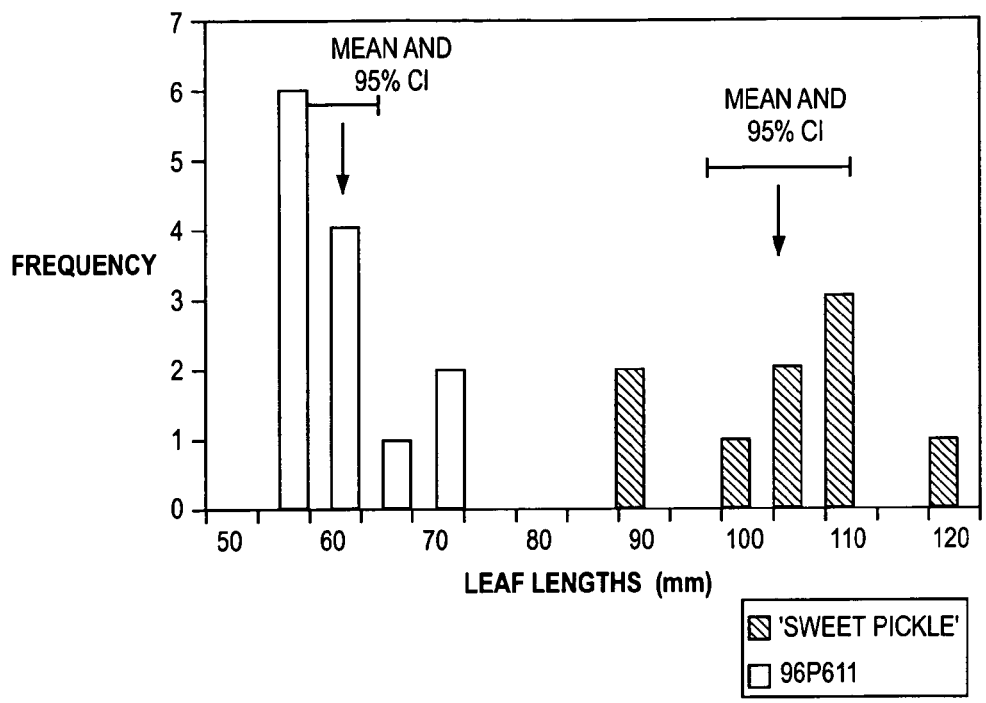

NON-PUNGENT ORNAMENTAL PEPPERS

RELATED APPLICATION INFORMATION

This application is a continuation-in-part of U.S. application Ser. No. 09/564,153 filed on May 3, 2000, now U.S. Pat. No. 7,087,819 which claims the benefit of U.S. application Ser. No. 60/132,389 filed on May 4, 1999, both of which are incorporated herein by reference.

FIELD OF THE INVENTION

The present invention relates to a novel gene complex which confers an ornamental phenotype and results in fruit that is non-pungent in pepper cultivars of the genus *Capsicum*.

This invention also relates to ornamental pepper seed, ornamental pepper plants, ornamental pepper varieties and ornamental pepper hybrids which contain this gene complex. In addition, the present invention also relates to methods for transferring this gene complex from sweet pepper varieties to ornamental pepper varieties and species and is useful for producing novel types and varieties of ornamental peppers which exhibit the ornamental phenotype and produce fruit that is phenotype.

BACKGROUND OF THE INVENTION

Within the genus *Capsicum*, several cultivars possess an aesthetic value for ornamental purposes in the garden and as indoor pot plants. Ornamental peppers can provide a range of pod shapes and colors complemented by varying degrees of green or purple foliage. Classification of ornamental peppers includes cultivars within three species: *Capsicum annuum* L., *Capsicum Chinese* Jacq., and *Capsicum pendulum* Willd. (See, Corley, W. L. and A. H. Dempsey. 1972. *Ornamental Pepper Evaluation* 1965-1971. University of Georgia College of Agriculture Experiment Stations Research Report 136:10 pp.).

Fruits of the ornamental peppers are edible but very pungent (See, Corley, W. L. and A. H. Dempsey, *Ornamental Pepper Evaluation* 1965-1971. University of Georgia College of Agriculture Experiment Stations Research Report 136:10 pp. (1972)). The pungent active ingredient found in peppers is the aromatic phenol capsaicin, which is capable of causing severe irritation. Capsaicin is produced by oil secreting glands located along the placenta. The presence or absence of pungency in *Capsicum* is reported to have simple trait inheritance with pungency partially dominant to non-pungency (See, Deshpande, R. B., *Indian Journal of Agricultural Science*, 5:513-516 (1945). The degree of pungency within a genotype is subject to unidentified genetic factors and the environment, in particular temperature (See, Lipper, L. F., et al., *The Botanical Review*, 32:24-55 (1966)).

Non-pungency is a characteristic of the Grossum Group of *Capsicum* annuum L. Var. annuum, containing the commonly known peppers Bell Pepper, Sweet Pepper or Green Pepper (*Hortus Third A Concise Dictionary of Plants Cultivated in the United States and Canada*, MacMillan Publishing Company 1976). It would be desirable to have non-pungent ornamental peppers thereby eliminating possible hazards from capsaicin in the landscape or indoor environment.

SUMMARY OF THE PRESENT INVENTION

The present invention relates to non-pungent ornamental *Capsicum* annuum plants or varieties which produce fruit (i.e., peppers), that contain capsaicin levels which are statistically equal to or less than the capsaicin levels of fruit (i.e., peppers) obtained from commercial sweet green *Capsicum annuum* plants at the $\alpha=0.05$ confidence level.

More specifically, in one embodiment, the present invention relates to *Capsicum annuum* plants that produce fruit that is non-pungent, meaning that said fruit has a capsaicin level no greater than 500 Scoville Heat Units. In addition, said plants have a height of less than about 29.0 cm. Moreover, in another embodiment, the present invention further relates to parts of these *Capsicum annum* plants, such as, but not limited to, seed, flowers, pollen, ovules, buds, shoots, cuttings, petals, leaves, stems, roots, tissues or combinations thereof.

The ornamental *Capsicum annuum* plants of the present invention contain a gene complex which confers the trait of non-pungency to the fruit produced by said plants. In addition, the ornamental *Capsicum annuum* plants exhibit an overall ornamental phenotype when compared to commercial sweet green *Capsicum annuum* plants. Examples of ornamental *Capsicum annuum* plants containing such a gene complex, which when expressed, confers non-pungency to the fruit and which have an overall ornamental phenotype, are the *Capsicum annuum* plants known as 96P601, 96P631, 96P610, 97P1938, 03P388-3,03P384-8 and PA47. The present invention also relates to parts such as, but not limited to, seed, flowers, pollen, ovules, buds, shoots, cuttings, petals, leaves, stems, roots, tissues or combinations thereof, produced by the non-pungent ornamental *Capsicum annuum* plants of the present invention. Moreover, the present invention also relates to a tissue culture comprising regenerable cells of the non-pungent ornamental *Capsicum annuum* plants of the present invention.

Additionally, in another embodiment, the present invention relates to ornamental *Capsicum annuum* seed containing a gene complex which when planted and regenerated into plants, produces a plant having an ornamental phenotype and which produces fruit that is non-pungent. Specifically, examples of ornamental pepper seed containing such a gene complex is seed obtained from *Capsicum annuum* plants known as 96P601, 96P631, 96P610, 97P1938, 03P388-3, 03P384-8 and PA47. The present invention also relates to ornamental *Capsicum annuum* plants produced by planting and growing seed of the present invention. These ornamental *Capsicum annuum* plants have an ornamental phenotype and produce fruit that contain capsaicin levels which are statistically equal to or less than the capsaicin levels of peppers obtained from commercial sweet green pepper *Capsicum annuum* plants at the $\alpha=0.05$ confidence level. More specifically, said fruit has a capsaicin level not greater than 500 Scoville Heat Units.

Also, in another embodiment, the present invention relates to non-pungent ornamental *Capsicum annuum* peppers (i.e., fruit) that have capsaicin levels which are statistically equal to or less than the capsaicin levels of peppers derived from commercial sweet green *Capsicum annuum* pepper cultivars at the $\alpha=0.05$ confidence level. More specifically, the non-pungent peppers of the present invention have a capsaicin level of not greater than 500 Scoville Heat Units.

In yet another embodiment, the present invention relates to a method for transferring one or more genes that confer non-pungency to fruit of a *Capsicum annuum* from sweet *Capsicum annuum* plants to ornamental *Capsicum annuum* plants. Methods for transferring such a gene or genes are well known in the art. For example, the method can involve the steps of crossing a non-pungent sweet non-ornamental or ornamental *Capsicum annuum* plant containing a gene for non-pungency with a pungent ornamental *Capsicum annuum* plant. Seeds resulting from this cross are then collected and regenerated into plants. *Capsicum annuum* plants containing a gene complex, namely those exhibiting an ornamental phenotype and that produce fruit that is non-pungent, are selected from the regenerated plants. The method also involves crossing the selected non-pungent ornamental *Capsicum annuum* plant containing this gene complex which confers non-pungency and ornamental attributes with other non-pungent ornamental peppers containing a gene complex which confers non-pungency and ornamental attributes or with pungent ornamental pepper plants having commercially desirable phenotypic traits for a sufficient number of generations to obtain a non-pungent ornamental pepper plant containing the gene complex which confers non-pungency and a desirable ornamental phenotype Additionally, in yet another embodiment, the present invention involves a method of producing *Capsicum annum* seed. The method involves a number of steps. One step involves crossing a first *Capsicum annuum* plant with a second *Capsicum annuum* plant and harvesting the resultant *Capsicum annuum* seed. Either the first or second *Capsicum annuum* plant is a *Capsicum annuum* plant having a height of less than about 29.0 cm and which produces fruit having a capsaicin level not greater than 500 Scoville Units or a part thereof or a descendant of a *Capsicum annuum* plant having a height of less than about 29.0 cm and which produces fruit having a capsaicin level not greater than 500 Scoville Units. The method further comprises the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. The method can further comprise the step of collecting the seed of the selected plant. The present invention also relates to a *Capsicum annuum* plant having a height of less than about 29.0 cm and which produces fruit having a capsaicin level not greater than 500 Scoville Units that is produced by the method described herein.

In still a further embodiment, the present invention also relates to a method of producing a *Capsicum annuum* plant in a pepper breeding program. The method can involve the following steps. The first step involves obtaining a *Capsicum annuum* plant having a height of less than about 29.0 cm and which produces fruit having a capsaicin level not greater than 500 Scoville Units or a part thereof or a descendant of a *Capsicum annuum* plant having a height of less than about 29.0 cm and which produces fruit having a capsaicin level not greater than 500 Scoville Units or a part thereof as a source of breeding material. The next step involves employing the above described *Capsicum annuum* plant as a source of plant breeding material in a plant breeding program using plant breeding techniques (including, but not limited to pedigree breeding, recurrent selection, backcrossing, or combinations of crossing, self-pollination and/or backcrossing) to produce a *Capsicum annuum* plant. Preferably, the *Capsicum annuum* plant produced and selected as a result of this method has a height of less than about 29.0 cm and produces fruit having a capsicin level not greater than 500 Scoville Units. The method can further comprise the step of collecting seed of the *Capsicum annuum* plant produced as a result of said method. The present invention also relates to a *Capsicum annuum* plant having a height of less than about 29.0 cm and which produces fruit having a capsaicin level not greater than 500 Scoville Units that is produced by the method described herein.

In yet another embodiment, the present invention relates to viable non-pungent ornamental *Capsicum annuum* seeds (1) designated 96P610, a representative sample of which have been deposited under ATCC Accession Number 203779; (2) designated 97P1938, a representative sample of which has been deposited under ATCC Accession Number PTA-5749; (3) designated P96P611, a representative sample of which has been deposited under ATCC Accession Number PTA-5689; and (4) designated PA47, a representative sample of which has been deposited under ATCC Accession Number The present invention further relates to plants grown from representative seeds designated 96P610, 97P1938, P96P611 or PA47 methods of using these plants in breeding to produce *Capsicum annuum* plants having an ornamental phenotype and which produce fruit that is non-pungent and *Capsicum annuum* plants having an ornamental phenotype and fruit that is non-pungent that are derived or have a pedigree that includes plants grown from seeds designated 96P610, 97P1938, P96P611 or PA47.

In still another embodiment, the present invention relates to a method of producing *Capsicum annuum* seed. The method comprises the following steps:

crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as 96P610, a representative sample of which is deposited under ATCC Accession Number 203779 or a descendant of the *Capsicum annuum* plant or a part thereof grown from seed designated as 96P610, a representative sample of which is deposited under ATCC Accession Number 203779.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing a *Capsicum annuum* plant in a pepper breeding program. The method comprises the following steps:

a) obtaining a *Capsicum annuum* plant or a part thereof grown from seed designated as 96P610, a representative sample of which is deposited under ATCC Accession Number 203779 or a descendant of the *Capsicum annuum* plant or a part thereof grown from seed designated as 96P610, a representative sample of which is deposited under ATCC Accession Number 203779, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing *Capsicum annuum* seed. The method comprises the following steps:

crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as 96P611, a representative sample of which is deposited under ATCC Accession Number PTA-5689 or a descendant of the *Capsicum annuum* plant or a part thereof grown from seed designated as 96P611, a representative sample of which is deposited under ATCC Accession Number PTA-5689.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing a *Capsicum annuum* plant in a pepper breeding program. The method comprises the following steps:

a) obtaining a *Capsicum annuum* plant or a part thereof grown from seed designated as 96P611, a representative sample of which is deposited under ATCC Accession Number PTA-5689 or a descendant of the *Capsicum annuum* plant or a part thereof grown from seed designated as 96P611, a representative sample of which is deposited under ATCC Accession Number PTA-5689, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing *Capsicum annuum* seed. The method comprises the following steps:

crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as 97P1938, a representative sample of which is deposited under ATCC Accession Number PTA-5749 or a descendant of the *Capsicum annuum* plant or a part thereof grown from seed designated as 97P1938, a representative sample of which is deposited under ATCC Accession Number PTA-5749.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing a *Capsicum annuum* plant in a pepper breeding program. The method comprises the following steps:

a) obtaining a *Capsicum annuum* plant or a part thereof grown from seed designated as 97P1938, a representative sample of which is deposited under ATCC Accession Number PTA-5749 or a descendant of the *Capsicum annuum* plant or a part thereof grown from seed designated as 97P1938, a representative sample of which is deposited under ATCC Accession Number PTA-5749, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In another embodiment, the present invention relates to a method of producing *Capsicum annuum* seed. The method comprises the following steps: crossing a first *Capsicum annuum* plant with a second *Capsicum annuum* plant and harvesting the resultant *Capsicum annuum* seed, wherein said first or second *Capsicum annuum* plant is a *Capsicum annuum* plant or a part thereof grown from seed designated as PA47, a representative sample of which is deposited under ATCC Accession Number or a descendant of the *Capsicum annuum* plant or a part thereof grown from seed designated as PA47, a representative sample of which is deposited under ATCC Accession Number.

This method can further comprise the step of planting the resultant *Capsicum annuum* seed and selecting a *Capsicum annuum* plant having a height equal to or less than about 29.0 cm or upright fruit wherein the capsaicin levels of said fruit is not greater than about 500 Scoville Heat Units. Additionally, the method can still further comprise the step of collecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

In yet still another embodiment, the present invention relates to a method of producing a *Capsicum annuum* plant in a pepper breeding program. The method comprises the following steps:

a) obtaining a *Capsicum annuum* plant or a part thereof grown from seed designated as PA47, a representative sample of which is deposited under ATCC Accession Number or a descendant of the *Capsicum annuum* plant or a part thereof grown from seed designated as PA47, a representative sample of which is deposited under ATCC Accession Number, as a source of breeding material; and b) employing the *Capsicum annuum* plant obtained in step a) as a source of plant breeding material in a plant breeding program using plant breeding techniques to produce a *Capsicum annuum* plant.

In the above method, the plant breeding techniques can be recurrent selection, backcrossing, pedigree breeding, combinations of these techniques or combinations of portions of these techniques. Additionally, the hereinbefore described method can further comprise the step of selecting a *Capsicum annuum* plant having a height equal to or less than about 29.0 cm or upright fruit wherein the capsaicin levels of said fruit is not greater than about 500 Scoville Heat Units. Additionally, the method can further comprise selecting the seed of the selected plant.

Additionally, the present invention also relates to a *Capsicum annuum* plant having a height of less than about 29.0 cm and which produces fruit having a capsaicin level not greater than 500 Scoville Units produced by this hereinbefore described method.

BRIEF DESCRIPTION OF THE FIGURES

FIG. 7 shows a comparison of the fruit weights of 'Sweet Pickle' and cultivar 96P611 of the present invention.

FIG. 8 shows a comparison of the leaf widths of 'Sweet Pickle' and cultivar 96P611 of the present invention.

FIG. 9 shows a comparison of the leaf lengths of 'Sweet Pickle' and cultivar 96P611 of the present invention.

DETAILED DESCRIPTION OF THE INVENTION

Figure 1:
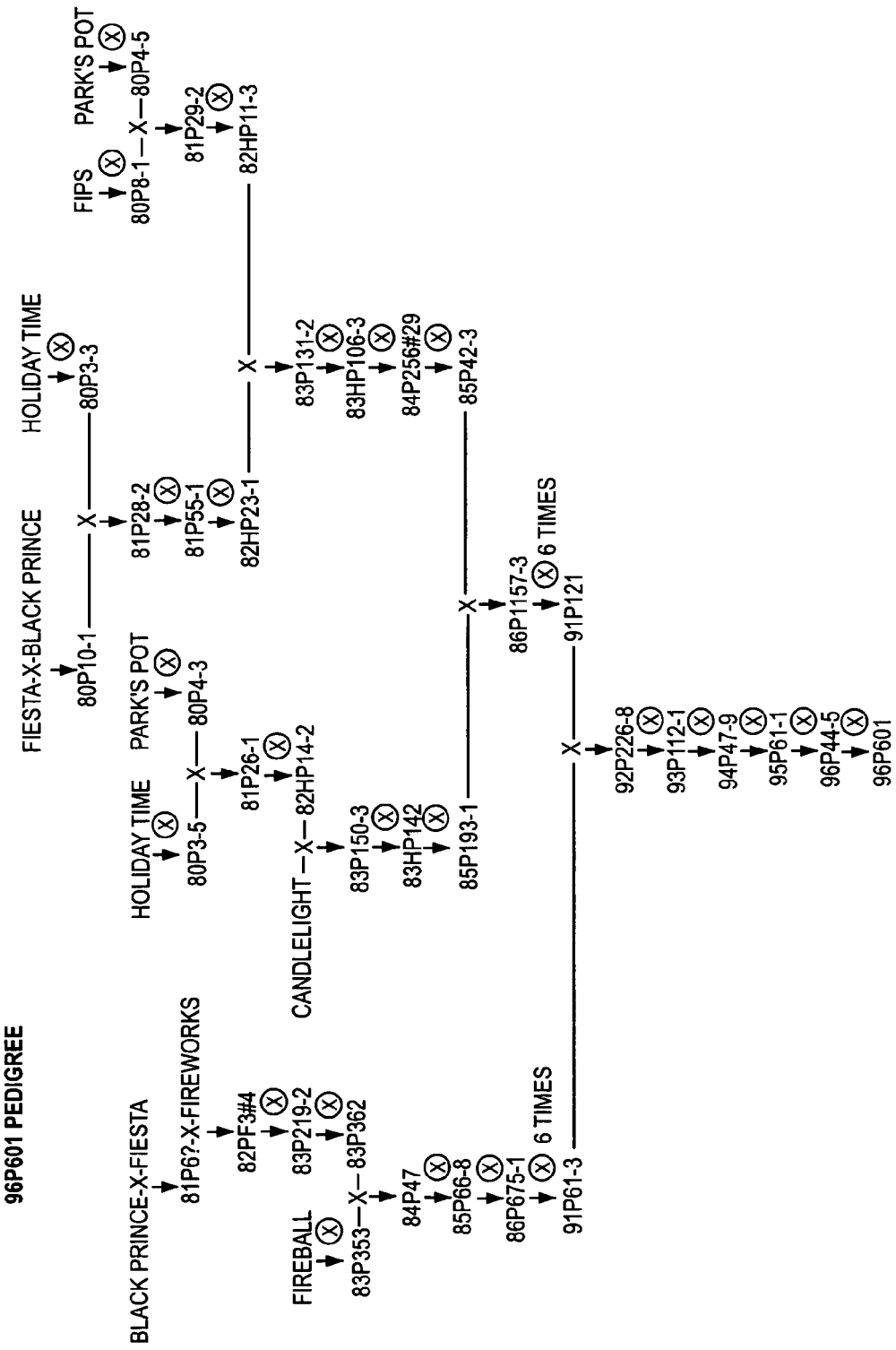
FIG. 1 shows the pedigree of *Capsicum annuum* cultivar 96P601 which has an ornamental phenotype and produces fruit that is non-pungent.

The present invention relates to ornamental *Capsicum annuum* plants that produce fruit (peppers) that are non-pungent. More specifically, the inventor of the present invention has discovered a transferable gene complex, which when introgressed into *Capsicum annuum* germplasm, results in the *Capsium annuum* plants of the present invention that exhibit an ornamental phenotype and that produce fruit (peppers) that are non-pungent. This gene complex can be incorporated into many other genetic backgrounds.

The terms "non-pungency" or "non-pungent" as used herein in connection with the *Capsicum annuum* fruit of the present invention refers to the level of capsaicin present in *Capsicum annuum* fruit as measured in Scoville Heat Units. Methods for determining the level of capsaicin in *Capsicum annuum* fruit is well known to those in the art and includes, but is not limited to, the use of high performance liquid chromatography (HPLC). *Capsicum annuum* fruit is considered to be "non-pungent" if the capsaicin levels in said fruit are statistically equal to or less than the capsaicin levels of fruit derived from a commercial sweet green Capsicum cultivar at the $\alpha=0.05$ confidence level. Sweet green *Capsicum annuum* fruit, while not produced for the ornamental market, can be used as a non-pungent benchmark based on their classification in the non-pungent *Capsicum grossum* Group (See *Hortus Third A Concise Dictionary of Plants Cultivated in the United States and Canada*, MacMillan Publishing Company 1976, herein incorporated by reference). More specifically, the *Capsicum annuum* fruit of the present invention contain a level of capsaicin that is not greater than 500 Scoville Heat Units.

As used herein, the terms "ornamental pepper plant", "ornamental *Capsicum annuum* plant" or "ornamental phenotype" refer to a *Capsicum annuum* plant possessing at least one ornamental characteristic, such as fruit number, fruit weight, plant height, branching, leaf length and leaf width, that is not statistically less desirable than those of commercially available pungent ornamental *Capsicum annuum* plants. Examples of pungent ornamental *Capsicum annuum* plants include, but are not limited to, 'Red Missile', 'Holiday Flame' and 'Masquerade' all available from Ball Horticultural Company, 622 Town Road, West Chicago, Ill., 60185. Preferably, the *Capsicum annuum* plants of the present invention have an ornamental phenotype that is illustrated by plants that exhibit a total plant height equal to or less than about 29.0 cm or upright, non-pungent fruit or a combination of upright, non-pungent fruit and a total plant height equal to or less than about 29.0 cm. For example, plants known as 96P610, 97P1938, P96P611, 03P388-3, 03P384-8, and PA47 which are described in more detail herein, each possess an ornamental phenotype and have a plant height equal to or less than about 29.0 cm, and upright, non-pungent fruit.

As used herein, the term "gene complex" refers a gene(s) or allele(s) which when introgressed or transferred into a *Capsicum annuum* plant that does not contain said gene(s) or allele(s) results in a *Capsicum annuum* plant produces a *Capsicum annuum* plant that has an ornamental phenotype and that produces fruit that is non-pungent. The gene complex described herein may be transferred into a *Capsicum annuum* plant which does not contain the gene complex using any techniques known in the art, such as by traditional breeding techniques (including, but not limited to, pedigree breeding, recurrent selection, backcrossing, etc.), mutagenesis, genetic transformation or engineering, combinations of crossing, self-pollination and/or backcrossing. Specifically, one or more genes comprising the gene complex can be inserted in the antisense direction in an expression construct using techniques well-known in the art, in order to "knock-out" capsaicin production.

The ornamental *Capsicum annuum* cultivars of the present invention are genetically stable. Additionally, the gene complex described herein can be bred into diverse ornamental *Capsicum* backgrounds, using any techniques known in the art, such as by traditional breeding techniques (including, but not limited to, pedigree breeding, recurrent selection, backcrossing, etc.), mutagenesis, genetic transformation or engineering, combinations of crossing, self-pollination and/or backcrossing.

As previously discussed, the *Capsicum annuum* plants of the present invention, which exhibit an ornamental phenotype and produce fruit that is non-pungent, are genetically stable, as evidenced by the stability of these traits through sexual crosses. Nonetheless, depending upon the cultivar, the level of capsaicin and thus the degree of pungency per fruit in a single a plant or in multiple plants may be adversely affected by environmental stress factors and may vary, without any variance in the genotype of the plant. Environmental stress factors which may adversely affect the level of capsaicin and thus degree of pungency per fruit include, but are not limited to, high temperatures, low soil fertility or water stress.

The non-pungent ornamental *Capsicum annuum* cultivars of the present invention maintain functional male and female organs, thus making the incorporation of the ornamental phenotype and the trait of non-pungency of the fruit into other ornamental pepper cultivars possible. The trait of non-pungency of the fruit may be incorporated into cultivars having a range of pod shapes and colors complemented by varying degrees of green or purple foliage.

It is expected that trait of non-pungency of the fruit can be predictably transferred into any ornamental *Capsicum* background using the techniques known in the art and described herein. For example, traditional breeding techniques such as, pedigree breeding, backcrossing and recurrent selection, for progeny having fruit that is non-pungent and an ornamental phenotype can be bred into diverse ornamental *Capsicum annuum* backgrounds. Intermating of superior genotypes which exhibit ornamental phenotypes and produce non-pungent fruit through repeated generations has resulted in the selection of cultivars with improved ornamental phenotypes that produce non-pungent fruit. Periodic outcrossing can be done during the breeding program in order to introduce desirable characteristics and to circumvent inbreeding depression.

It is expected that any selected *Capsicum annuum* pepper cultivar having an ornamental phenotype and that produces non-pungent fruit can be produced as progeny from sexual crosses and sold as seed. Methods for the storage of such seed are well known in the art.

The present invention also relates to a method of transferring a gene for non-pungency of the fruit from a sweet pepper plant to a pungent ornamental pepper plant. The method involves the steps of crossing a sweet pepper plant containing a gene for non-pungency of the fruit with a pungent ornamental pepper plant. The seeds resulting from the cross are collected, planted and regenerated into plants. Non-pungent ornamental pepper plants which contain the gene complex which confers non-pungency to the fruit and an ornamental phenotype are then selected from the regenerated plants. In addition, the method further involves crossing the selected non-pungent ornamental pepper plants containing the gene complex which confers non-pungency to the fruit and an ornamental phenotype with other non-pungent ornamental pepper plants containing the gene complex which confers non-pungency to the fruit and an ornamental phenotype or with pungent ornamental pepper plants having commercially desirable phenotypic traits for a sufficient number of generations, to obtain non-pungent ornamental pepper plants containing the gene complex which confers non-pungency to the fruit and a desirable ornamental phenotype.

This previously unknown non-pungent ornamental pepper characteristic arose from breeding and research efforts. The gene that encodes for non-pungent fruit originated from two sweet green pepper sources, which are identified as 'Park's Pot' and 'California Wonder'. 'Park's Pot' is a bell pepper cultivar that was intended for pot plant culture and has large, bell-shaped fruit and is commercially available from Geo. W. Park Seed Co. Inc., 1 Parkton Avenue, Greenwood, S.C., 29647. 'California Wonder' has large, green, pendent, sweet, three to four lobed, bell-shaped peppers and is commercially available from The Pepper Gal, P.O. Box 23006, Fort Lauderdale, Fla. 33311.

By way of example, and not of limitation, examples of the present invention will now be given.

EXAMPLE 1

Pedigree for Non-Pungent Ornamental Pepper Cultivar 96P601

FIG. 1 shows the pedigree that lead to non-pungent ornamental *Capsicum annuum* cultivar 96P601. Plants of 96P601 have a height that is less than or equal to 29.0 cm and fruit that is non-pungent. More specifically, the fruit produced by plants of *Capsicum annuum* plant 96P601 have a capsaicin level not greater than 500 Scoville Heat Units. Plants of 96P601 or parts from this plant, such as parts of these *Capsicum annum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, 96P601 can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 96P601 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new, stable *Capsicum annuum* plants having a height equal to or less than about 29.0 cm and that have fruit having capsaicin levels not greater than about 500 Scoville Heat Units.

EXAMPLE 2

Pedigree for Non-Pungent Ornamental Pepper Cultivar 96P631

Figure 2:
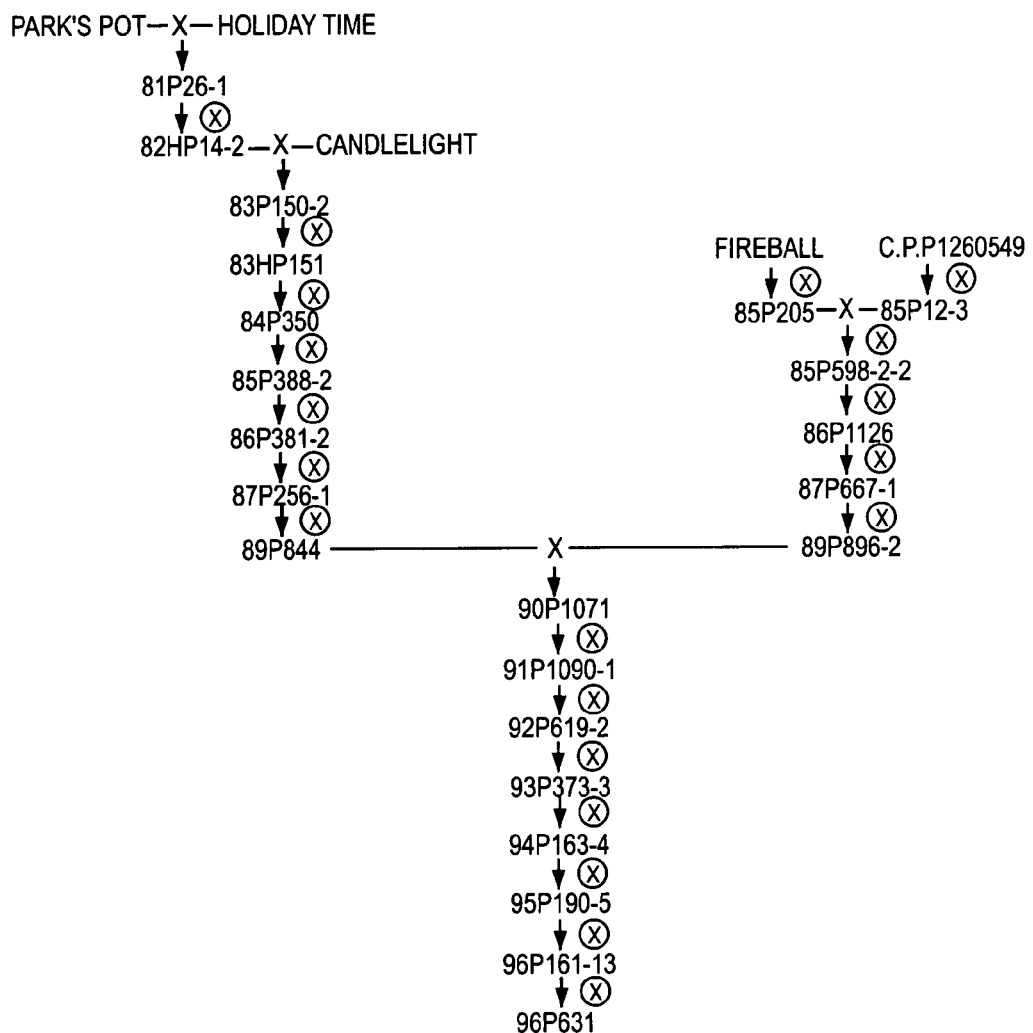
FIG. 2 shows the pedigree of *Capsicum annuum* cultivar 96P631 which has an ornamental phenotype and produces fruit that is non-pungent.

FIG. 2 shows the pedigree that lead to non-pungent ornamental *Capsicum annuum* cultivar 96P631. Plants of 96P631 have a height that is less than or equal to 29.0 cm and fruit that is non-pungent. More specifically, the fruit produced by plants of *Capsicum annuum* plant 96P631 have a capsaicin level not greater than 500 Scoville Heat Units. Plants of 96P631 or parts from this plant, such as parts of these *Capsicum annum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, pollen obtained from 96P631 can be placed on the stigma of a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 96P631 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

EXAMPLE 3

Pedigree for Non-Pungent Ornamental Pepper Cultivar 96P610

Figure 3:
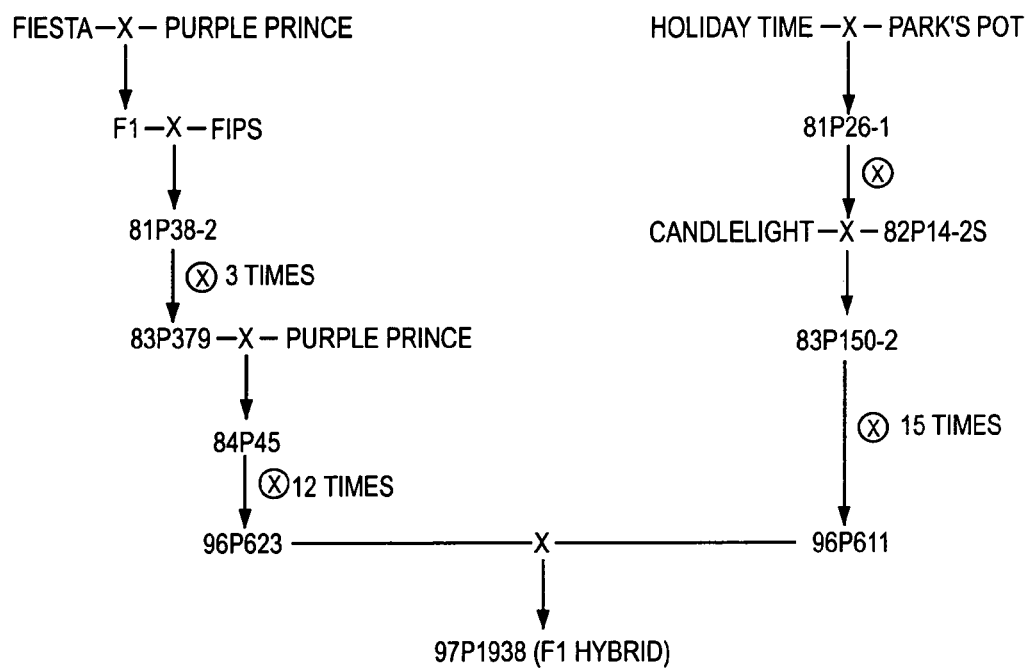
FIG. 3 shows the pedigree of *Capsicum annuum* cultivar 96P1938 which has an ornamental phenotype and produces fruit that is non-pungent.

FIG. 3 shows the pedigree that lead to non-pungent ornamental *Capsicum annuum* cultivar 96P610. As discussed in more detail herein, representative seed of 96P610 has been deposited with the ATCC. Plants grown from this seed produce *Capsicum annuum* plants that have a height that is less than or equal to 29.0 cm and fruit that is non-pungent. More specifically, the fruit produced by plants of *Capsicum annuum* plant 96P610 have a capsaicin level not greater than 500 Scoville Heat Units. Plants of 96P610 or parts from this plant, such as parts of these *Capsicum annum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, 96P610 can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 96P610 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

EXAMPLE 4

Pedigree for Non-Pungent Ornamental Pepper Cultivar 97P1938

Figure 4:
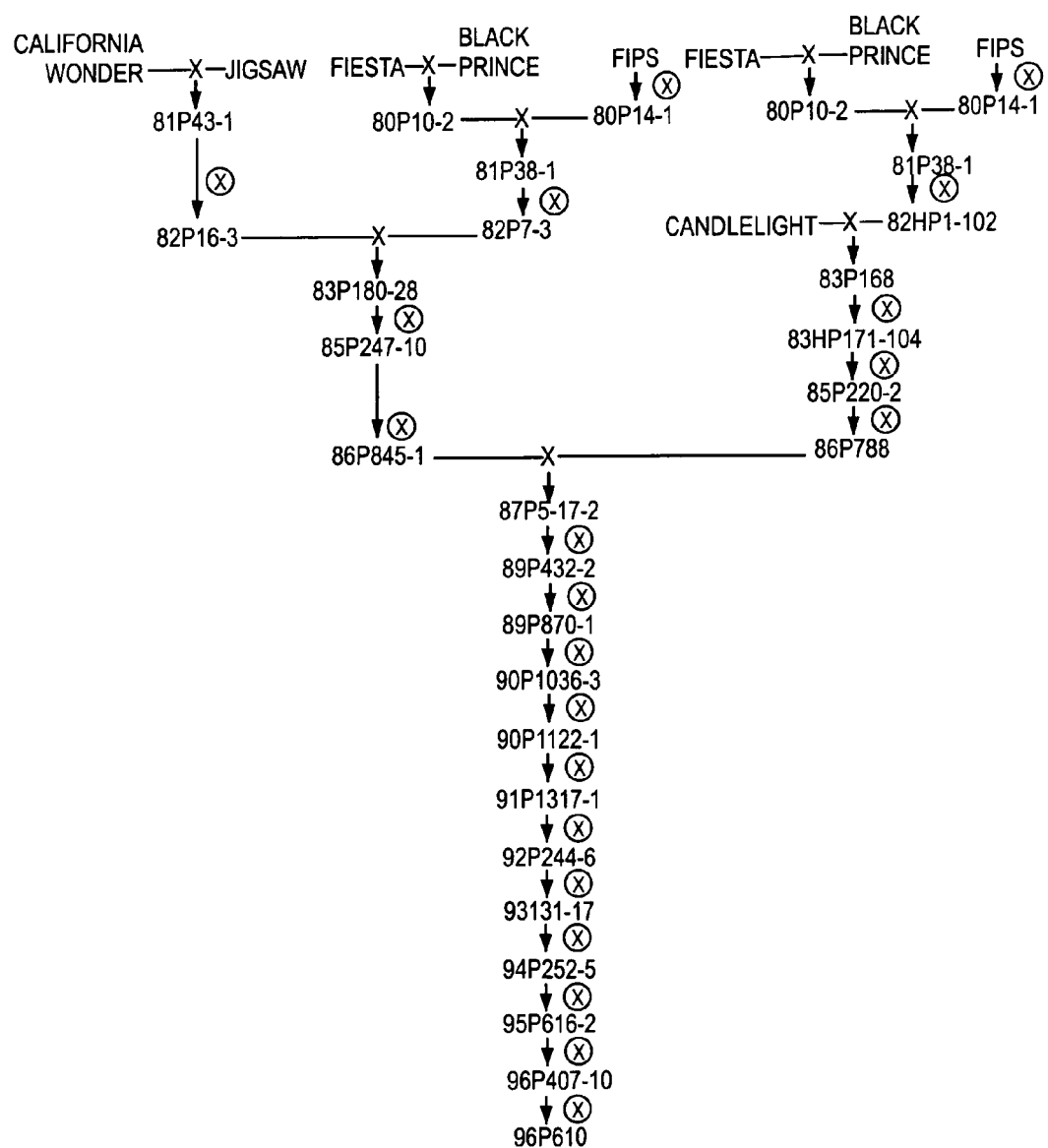
FIG. 4 shows the pedigree of *Capsicum annuum* cultivar 96P610 which has an ornamental phenotype and produces fruit that is non-pungent.

FIG. 4 shows the pedigree that lead to non-pungent ornamental *Capsicum annuum* cultivar 97P1938. As discussed in more detail herein, representative seed of 97P1938 has been deposited with the ATCC. Plants grown from this seed produce *Capsicum annuum* plants that have a height that is less than or equal to 29.0 cm and fruit that is non-pungent. More specifically, the fruit produced by plants of *Capsicum annuum* plant 97P1938 have a capsaicin level not greater than 500 Scoville Heat Units. Plants of 97P1938 or parts from this plant, such as parts of these *Capsicum annum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, plants of 97P1938 can self-pollinated (also referred to as being "selfed" or "selfing") After said selfing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 97P1938 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant can self-pollinated. After said selfing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

EXAMPLE 5

Pedigree for Non-Pungent Ornamental Pepper Cultivar 03P388-3

Figure 5:
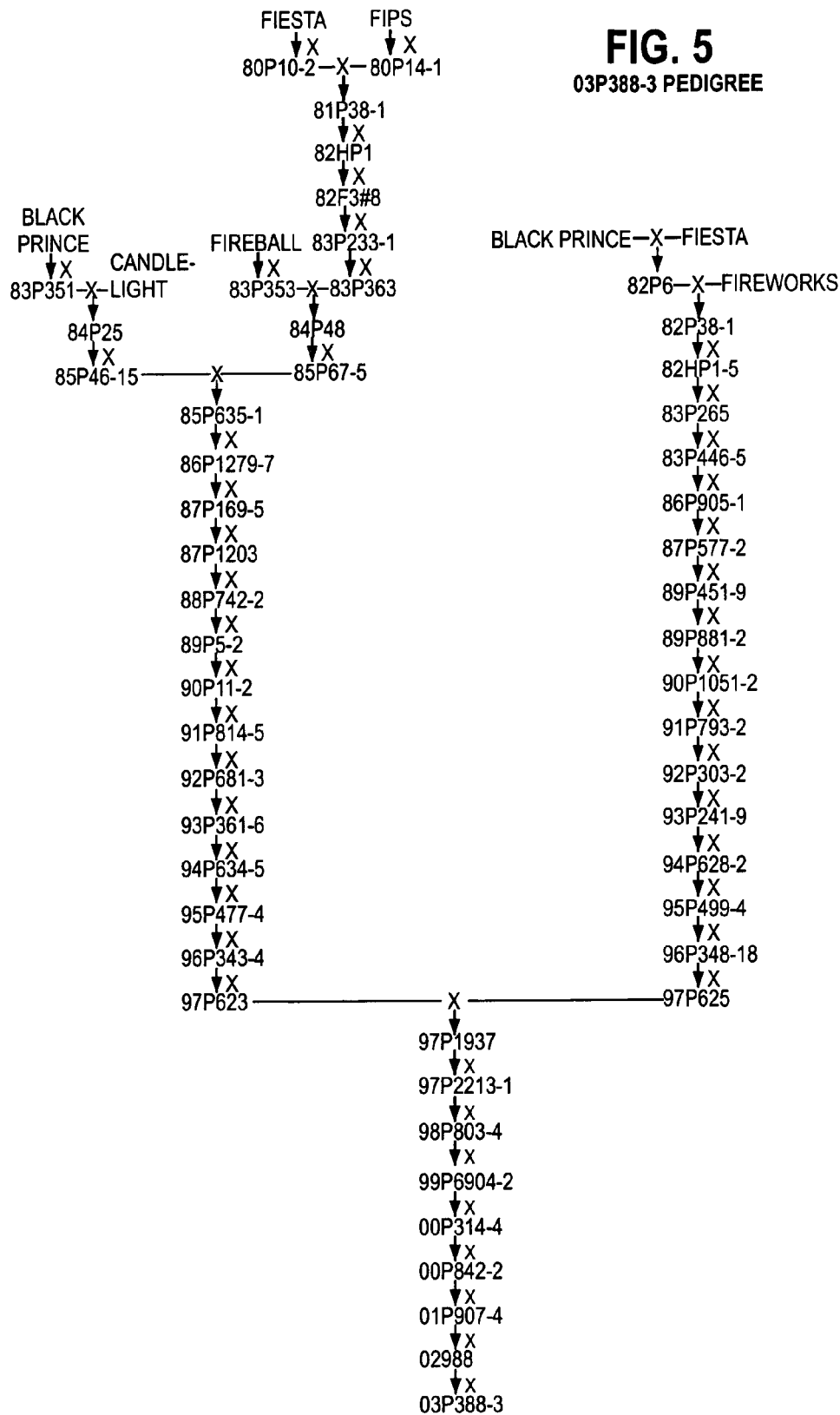
FIG. 5 shows the pedigree of *Capsicum annuum* cultivar 03P388-3 which has an ornamental phenotype and produces fruit that is non-pungent.

FIG. 5 shows the pedigree that lead to non-pungent ornamental *Capsicum annuum* cultivar 03P388-3. Plants of 03P388-3 have a height that is less than or equal to 29.0 cm and fruit that is non-pungent. More specifically, the fruit produced by plants of *Capsicum annuum* plant 03P388-3 have a capsaicin level not greater than 500 Scoville Heat Units. Plants of 03P388-3 or parts from this plant, such as parts of these *Capsicum annum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, 03P388-3 can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 03P388-3 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as a part from a Descendant, such as parts of these *Capsicum annum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected (hereinafter referred to as "Second Descendant(s)"). Methods for determining the levels of capsaicin in fruit, such as a pepper, are well known to those skilled in the art.

The Second Descendants selected above that have a height equal to or less than about 29.0 cm and that have fruit having capsaicin levels not greater than about 500 Scoville Heat Units can be used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Second Descendant or a part from a Second Descendant, such as parts of these *Capsicum annum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

EXAMPLE 6

Pedigree for Non-Pungent Ornamental Pepper Cultivar 03P384-8

Figure 6:
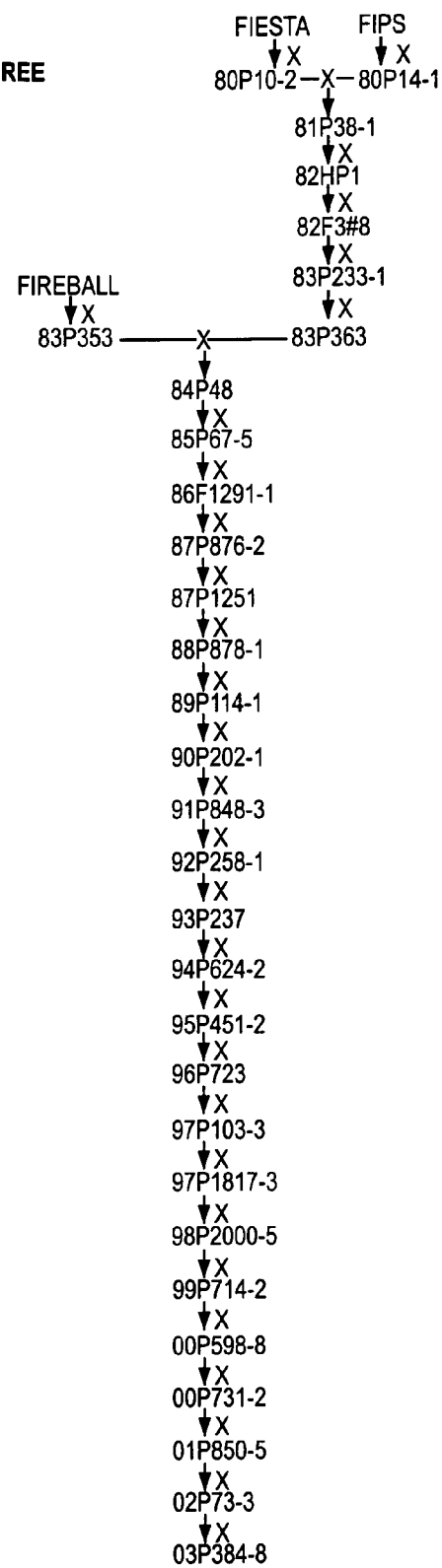
FIG. 6 shows the pedigree of *Capsicum annuum* cultivar 03P384-8 which has an ornamental phenotype and produces fruit that is non-pungent.

FIG. 6 shows the pedigree that lead to non-pungent ornamental *Capsicum annuum* cultivar 03P384-8. Plants of 03P384-8 have a height that is less than or equal to 29.0 cm and fruit that is non-pungent. More specifically, the fruit produced by plants of *Capsicum annuum* plant 03P384-8 have a capsaicin level not greater than about 500 Scoville Heat Units. Plants of 03P384-8 or parts from this plant, such as parts of these *Capsicum annum* plants, such as, but not limited to, seed, flowers, pollen, ovules, buds, shoots, cuttings, petals, leaves, stems, roots, tissues or combinations thereof, can be used in produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, pollen from 03P384-8 can be placed on the stigma of a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. Methods for determining the levels of capsaicin in fruit, such as a pepper, are well known to those skilled in the art.

Plants that have a height equal to or less than about 29.0 cm and that have fruit having capsaicin levels not greater than about 500 Scoville Heat Units, that are produced by the above method and that are selected, are considered to be descendants of 03P384-8 (hereinafter referred to as "Descendant(s)"). Such Descendants can used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a Descendant or a part from a Descendant, such as parts of these *Capsicum annum* plants, such as, but not limited to, seed, flowers, pollen, ovules, buds, shoots, cuttings, petals, leaves, stems, roots, tissues or combinations thereof, can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected (hereinafter referred to as "Second Descendant(s)"). Methods for determining the levels of capsaicin in fruit, such as a pepper, are well known to those skilled in the art.

The Second Descendants selected above that have a height equal to or less than about 29.0 cm and that have fruit having capsaicin levels not greater than about 500 Scoville Heat Units can be used to produce new *Capsicum annuum* plants having a height less than or equal to 29.0 cm and fruit that is non-pungent. Techniques for producing such new *Capsicum annuum* plants are well known to those skilled in the art and include the use of traditional plant breeding techniques, such as pedigree breeding, recurrent selection or backcrossing, or genetic transformation or engineering, or combinations of crossing, self-pollination and/or backcrossing. For example, a cutting from a Second Descendant can be crossed, as either a male or female parent plant with a second *Capsicum annuum* plant. After said crossing, the resulting *Capsicum annuum* seed is harvested and grown into *Capsicum annuum* plants. *Capsicum annuum* plants which have height equal to or less than about 29.0 cm and that have fruit having capsaicin levels not greater than about 500 Scoville Heat Units are then selected. As those skilled in the art can appreciate, such breeding and selection methods described above can be repeated over and over to produce a variety of new *Capsicum annuum* plants having a height equal to or less than about 29.0 cm and that have fruit having capsaicin levels not greater than about 500 Scoville Heat Units.

EXAMPLE 7

Evaluation of Capsaicin in Ornamental Pepper Cultivars

To evaluate the degree of pungency, capsaicin levels, as measured in Scoville Heat Units, were determined. For capsaicin analysis, fruit from ten pepper varieties were collected from greenhouse-grown material, and a commercial Sweet Green pepper was purchased locally. Plants were grown in a 1999 trial at Pan American Seed Company located in Elburn, Ill.

Included in the analysis were non-pungent ornamental peppers obtained from the plants described herein, specifically, 96P601, 96P610, 96P631 and 97P1938. Selection 96P611 is a parent of the hybrid pepper 97P1938. The varieties 'Red Missile', 'Masquerade' and 'Holiday Flame' were used as commercial ornamental pepper controls. Also evaluated was 'Triton', which is a non-pungent pepper marketed by Ball Horticultural Company, and A PI 'Sweet Orange' which was referred to in a publication as being a non-pungent ornamental pepper with "good ornamental characteristics" (See, Corley, W. L. and A. H. Dempsey, Ornamental Pepper Evaluation 1965-1971. University of Georgia College Agriculture Experiment Stations Research Report 136: 10 pp. (1972)).

For analysis, the pepper fruit were dried at 40° C. Three whole pepper fruits from three separate plants of each variety were ground into a fine powder and 200 mg was weighed and collected in a 5 ml tube. Two milliliters (mls) of methanol were added and mixed for 1 minute using a Prohomogenizer. The mixture was centrifuged and the supernatant passed through a 0.2 μm filter. Capsaicin levels were measured using HPLC. Samples of 50 μl were injected into a Supelcosil LC-18 25 cm×4.6 mm column and run at 1.5 ml/minute for 26 minutes using 60/40, methanol/water. Conditions and separation techniques followed the method of T. Cooper et al., *J. Agric. Food Chem.*, 39, 2253-2256 (1991). The results are shown below in Table 1.

TABLE 1

| Variety | Average Scoville Heat Units | Tukey Grouping ($\alpha = 0.05$) |
|---|---|---|
| Sweet Green pepper | 96.8 | C |
| 'Red Missile' | 19708.3 | AB |
| 'Masquerade' | 36799.2 | A |
| 'Holiday Flame' | 34043.4 | A |
| 96P601 | 175.4 | C |
| 96P610 | 128.1 | C |
| 97P631 | 191.9 | C |
| 97P1938 | 121.9 | C |
| 96P611 | 137.9 | C |
| 'Triton' | 113.8 | C |
| 'Sweet Orange' | 5768.4 | B |

Analysis was completed using Tukey's Studentized Range Test and logarithmic transformed values of the original data. The analysis identified no significant difference between the Sweet Green pepper, 96P601, 96P610, 96P631, 97P1938, 96P611 or 'Triton'. The PI 'Sweet Orange' had a significantly higher capsaicin level than the ornamental peppers of the present invention, indicating that 'Sweet Orange' should not be classified as being non-pungent. The capsaicin levels of all non-pungent selections tested were significantly lower than the pungent ornamental controls 'Red Missile', 'Masquerade' and 'Holiday Flame'.

EXAMPLE 8

Comparison of Ornamental Characteristics of Non-Pungent and Pungent Peppers

Six greenhouse plants of each cultivar listed in Table 2, below, were evaluated for fruit number, fruit weight, height, lateral branches, leaf length and leaf width. For fruit weight, five fruit from each of six plants were individually weighed and an average weight per plant was analyzed. For leaf length and leaf width, five mature basal leaves were measured and an average measurement per plant was analyzed. The three commercial pungent cultivars 'Red Missile', 'Holiday Flame' and 'Masquerade' were randomly selected. Plants were grown in a 1999 trial at PanAmerican Seed Company located in Elburn, Ill. Means were compared using the Least Significant Different Test ($\alpha$=0.05). All non-pungent cultivars of the present invention possess ornamental characteristics that are statistically equivalent or superior to the commercial pungent ornamental peppers. In contrast, 'Triton' a non-pungent *Capsicum annuum* marketed by Ball Horticultural Company, does not possess the desirable phenotype of the commercial pungent ornamental *Capsicum annuum* plants. It has significantly less and larger fruit, it is significantly less branched, and has significantly longer and wider leaves than the commercial pungent ornamental *Capsicum annuum* plants. A PI 'Sweet Orange' was referred to in a publication as being a non-pungent ornamental *Capsicum annuum* plant which had "good ornamental characteristics" (See, Corley, W. L. and A. H. Dempsey, Ornamental Pepper Evaluation 1965-1971. University of Georgia College of Agriculture Experiment Stations Research Report 136: 10 pp. (1972)). The ornamental characteristics of 'Sweet Orange' are statistically less desirable than commercial pungent ornamental *Capsicum annuum* plants for all characteristics evaluated.

TABLE 2

| Variety | Fruit Number | 5% LSD LSD = 9.4 | Fruit Weight (g) | 5% LSD LSD = 1.5 | Plant Height (cm) | 5% LSD LSD = 2.8 |
|---|---|---|---|---|---|---|
| 'Red Missile' | 51.7 +/− 4.9 | bc | 0.9 +/− 0.2 | a | 18.6 +/− 1.7 | b |
| 'Masquerade' | 63.5 +/− 7.5 | d | 1.9 +/− 0.1 | a | 29.3 +/− 2.8 | d |
| 'Holiday Flame' | 55.8 +/− 10.3 | cd | 1.8 +/− 0.3 | a | 18.7 +/− 2.7 | b |
| 96P601 | 44.5 +/− 4.3 | b | 1.1 +/− 0.1 | a | 9.8 +/− 0.5 | a |
| 96P610 | 59.5 +/− 2.7 | cd | 0.8 +/− 0.1 | a | 8.9 +/− 0.9 | a |
| 96P631 | 83.2 +/− 15.1 | e | 0.9 +/− 0.1 | a | 19 +/− 1.3 | b |
| 97P1938 | 95.2 +/− 12.3 | ef | 1.1 +/− 0.1 | a | 26 +/− 2.8 | c |
| 'Triton' | 7.8 +/− 1.5 | a | 14.1 +/− 2.5 | c | 18.5 +/− 2.2 | b |
| 'Sweet Orange' | 10.5 +/− 5.7 | a | 10.6 +/− 3.0 | b | 35.5 +/− 4.6 | e |

| Variety | Lateral Branches | 5% LSD LSD = 1.2 | Leaf Length (cm) | 5% LSD LSD = 0.7 | Leaf Width (cm) | 5% LSD LSD = 0.4 |
|---|---|---|---|---|---|---|
| 'Red Missile' | 9.3 +/− 1.2 | e | 8.2 +/− 0.4 | d | 4.0 +/− 0.2 | c |

TABLE 2-continued

| | | | | | | | |
|---|---|---|---|---|---|---|---|
| 'Masquerade' | 7.3 +/− 1.5 | c | 7.1 +/− 0.2 | bc | 3.3 +/− 0.1 | b | |
| 'Holiday Flame' | 7.3 +/− 1.0 | c | 7.6 +/− 0.6 | cd | 3.2 +/− 0.2 | b | |
| 96P601 | 7.7 +/− 0.5 | cd | 5.8 +/− 0.3 | a | 2.3 +/− 0.1 | a | |
| 96P610 | 9.5 +/− 1.2 | e | 6.1 +/− 0.1 | a | 2.6 +/− 0.2 | a | |
| 96P631 | 8.8 +/− 0.8 | de | 5.5 +/− 0.3 | a | 2.4 +/− 0.1 | a | |
| 97P1938 | 11.8 +/− 1.2 | c | 7.0 +/− 0.4 | bc | 3.2 +/− 0.2 | b | |
| 'Triton' | 2.3 +/− 0.5 | a | 11.4 +/− 1.1 | e | 5.8 +/− 0.4 | e | |
| 'Sweet Orange' | 3.7 +/− 0.8 | b | 11.0 +/− 1.3 | e | 4.9 +/− 0.7 | d | |

EXAMPLE 9

Comparison of 'Sweet Pickle' and 96P611 Ornamental Characteristics

The ornamental characteristics of 96P611, hybrid parent of 97P 1938 of the present invention, were compared to 'Sweet Pickle' a non-pungent salad pepper marketed by Geo. W. Park Seed Co. Inc., 1 Parkton Avenue, Greenwood, S.C., 29647 using field grown plants from two replicated plots. Samples were evaluated for fruit weight, leaf width and leaf length. ANOVA results determined that differences between replicates were non-signifcant. Variation within samples from each variety was used to establish confidence intervals. As shown in FIGS. 7-9, cultivar 96P611 possesses the superior ornamental characteristics of smaller fruit weight and leave size when compared to 'Sweet Pickle'.

EXAMPLE 10

Non-Pungent Ornamental Pepper Breeding

As discussed previously herein, all *Capsicum annuum* plants of the present invention, which have an ornamental phenotype and produce fruit that is non-pungent, maintain functional male and female sexual flower parts and can be used in breeding programs employing techniques that are well known to those skilled in the art, including, but not limited to, traditional plant breeding techniques, such as pedigree breeding, recurrent selection or backcrossing, or genetic transformation or engineering, or breeding processes involving combinations of crossing, self-pollination and/or backcrossing. In particular, plants of *Capsicum annuum* 96P610 were crossed (96P610 was used as a male parent) with plants of *Capsicum annuum* cultivar 03P388-3 (which was used as a female parent). The resulting seeds produced from this cross were selected. The seeds were planted and grown into plants. Then, *Capsicum annuum* plant 05P440 was selected. Plant 05P440 has ornamental characteristics, with non-pungent fruit (namely, the fruit have a capsaicin level of not greater than 500 Scoville Units), yellow immature fruit that turn red at maturity and a plant height of approximately 19 cm (from the soil line).

The pedigree of female parent 03P388-3 is described in FIG. 5. In addition to being used in the above described cross, 03P388-3 is a parent of *Capsicum annuum* plant PA47 of the present invention. *Capsicum annuum* plant PA47 has an ornamental phenotype, namely, it has a height less than or equal to 29.0 cm (See Table 3 below). In addition, it has a mounded and spreading growth habit with purple conical fruit that mature to red.

TABLE 3

| Ornamental Traits | Measurement (cm) |
|---|---|
| Plant Height (from soil line) | 20.9 |
| Plant width | 66.7 |
| Leaf length (including petiole) | 6.8 |
| Leaf width | 2.0 |

The data in Table 3 above, was averaged from 10 plants grown in a summer field trial at Elburn, Ill. in 2005. In addition, approximately 20 grams of whole peppers from three plants of PA47 were sent to Silliker, Inc. for Scoville Heat Test analysis. Each sample was determined to have a capsaicin level of less than 1 Scoville Heat Unit.

The *Capsicum annuum* commercial hybrid 97P1938 of the present invention, which has an ornamental phenotype and produces fruit that is non-pungent, is the direct progenitor of several experimental lines currently being trialed for commercialization, including *Capsicum annuum* lines, 05P453, 05P454and 05P605. These descendants of 97P1938 all haven an ornamental phenotype and produce fruit that is non-pungent. These lines were developed from several years of selfing and selection from the original hybrid, 97P1938. These progeny are non-pungent, range from 19 to 34 cm in plant height and have long-conical to conical fruit that are yellow or purple in immature fruit color, maturing to red.

As shown in FIG. 4, the *Capsicum annuum* hybrid 97P1938 is the result of a cross between *Capsicum annuum* 96P623×*Capsicum annuum* 96P611. Parent line 96P611 continues to maintain functional male and female sexual flower parts and as exemplified herein, can be used to create not only the commercial hybrid 97P1938, but other new *Capsicum annuum* plants that have ornamental phenotypes and fruit that is non-pungent (namely, the fruit have a capsaicin level of not greater than 500 Scoville Units).

The parents of *Capsicum annuum* hybrid PA47 of the present invention, which has an ornamental phenotype and has fruit that is non-pungent, is the result of a cross between *Capsicum annuum* plant 03P388-3, shown in FIG. 5, and *Capsicum annuum* plant 03P384-8, shown in FIG. 6. PA47 is deemed to be a commercial hybrid and is being used in a variety of breeding programs and is producing a number of descendants that exhibit an ornamental breeding phenotype and has fruit that is non-pungent. More specifically, PA47 has been self-pollinated. The seed resulting from this self-pollination have been collected. This seed was planted and a plant identified as 05P443 was selected. Line 05P443 is an experimental line that has an ornamental phenotype and produces brilliant purple fruit that are non-pungent (namely, the fruit have a capsaicin level of not greater than 500 Scoville Units). Characteristics of progeny from this pedigree are shown below in Table 4.

TABLE 4

| Selection | Plant width (cm) | Plant height (cm) | Leaf length (mm) | Leaf width (mm) | Fruit length (mm) | Fruit width (mm) |
|---|---|---|---|---|---|---|
| 453-3 | 48 | 34 | 43 | 18 | 50 | 7 |
| 454-2 | 41 | 28 | 49 | 19 | 36 | 10 |
| 605-1 | 36 | 19 | 39 | 18 | 35 | 8 |
| 440-1 | 25 | 19 | 50 | 18 | 48 | 11 |
| 443-3 | 61 | 28 | 32 | 14 | 38 | 9 |
| 443-9 | 33 | 15 | 41 | 18 | 38 | 13 |
| 368-1 | 46 | 20 | 25 | 12 | 18 | 6 |
| 418-5 | 23 | 15 | 36 | 17 | 52 | 7 |
| 427-5 | 36 | 17 | 28 | 11 | 16 | 8 |
| 428-1 | 43 | 18 | 27 | 10 | 14 | 10 |
| 514-1 | 71 | 28 | 39 | 20 | 22 | 12 |
| 520-1 | 30 | 15 | 35 | 18 | 27 | 8 |
| 520-2 | 46 | 18 | 32 | 13 | 30 | 5 |
| 523-3 | 28 | 17 | 45 | 16 | 42 | 6 |
| 524-3 | 30 | 24 | 41 | 18 | 38 | 5 |
| 544-1 | 41 | 11 | 22 | 9 | 16 | 8 |
| 553-4 | 41 | 15 | 32 | 11 | 40 | 8 |
| 558-4 | 56 | 24 | 28 | 12 | 19 | 8 |
| 574-5 | 71 | 33 | 33 | 14 | 28 | 8 |
| 590-6 | 30 | 18 | 28 | 12 | 28 | 7 |
| 590-7 | 33 | 15 | 32 | 14 | 40 | 7 |
| 610-10 | 33 | 18 | 40 | 15 | 25 | 8 |
| 616-1 | 33 | 18 | 44 | 16 | 38 | 5 |

Presently, there are 44 *Capsicum annuum* experimental lines that are descendents from other crosses involving the parent 03P384-8. Each of these experimental lines has an ornamental phenotype and produce fruit that are non-pungent (namely, the fruit have a capsaicin level of not more than 500 Scoville Units). There are also six (6) *Capsicum annuum* lines that are descendants of crosses involving the other parent, PA47. Each of these six *Capsicum annuum* lines have an ornamental phenotype and produce fruit that are non-pungent (namely, the fruit have a capsaicin level of not greater than 500 Scoville Units). These progeny range from 11 to 33 cm in plant height, have non-pungent fruit and exhibit extremely high fruitfulness as was characteristic of their parent (progeny range from having in excess of 95 to 600 fruit per plant).

From past and current breeding, it is abundantly clear that the *Capsicum annuum* plants of the present invention that have an ornamental phenotype and that produce fruit that is non-pungent are extremely useful in the breeding of subsequent lines (namely, descendants) of *Capsicum annuum* plants that have an ornamental phenotype and that produce fruit that is non-pungent. Using them as a source of plant breeding material in a plant breeding program for non-pungent ornamental peppers provides much more ornamental and promising progeny and a better breeding outcome than does the use of other non-pungent edible types as a donor of non-pungency. Hundreds of derivatives or descendants from these crosses have advanced through the breeding program and many persist today, on their way to being the subsequent generation of commercialized *Capsicum annuum* plants have an ornamental phenotype and fruit that is non-pungent.

DEPOSIT INFORMATION

Two thousand five hundred (2500) seeds of *Capsicum annuum* plant PA47 which exhibits an ornamental phenotype and produces fruit that is non-pungent have been placed on deposit with the American Type Culture Collection (ATCC), 10801 University Blvd., Manassas, Va., 20110-2209 under Deposit Accession Number PTA-8808 on Dec. 5. 2007. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. These *Capsicum annuum* seeds will be replenished should it become non-viable at the depository.

Two thousand five hundred (2500) seeds of *Capsicum annuum* plant 97P1938 which exhibits an ornamental phenotype and produces fruit that is non-pungent have been placed on deposit with the American Type Culture Collection (ATCC), 10801 University Blvd., Manassas, Va., 20110-2209 under Deposit Accession Number PTA-5749 on Jan. 7, 2004. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. These *Capsicum annuum* seeds will be replenished should it become non-viable at the depository.

Two thousand five hundred (2500) seeds of *Capsicum annuum* plant 96P611 which exhibits an ornamental phenotype and produces fruit that is non-pungent have been placed on deposit with the American Type Culture Collection (ATCC), 10801 University Blvd., Manassas, Va., 20110-2209 under Deposit Accession Number PTA-5689 on Dec. 8, 2003. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. These *Capsicum annuum* seeds will be replenished should it become non-viable at the depository.

Two thousand five hundred (2500) seeds of *Capsicum annuum* plant PA47 which exhibits an ornamental phenotype and produces fruit that is non-pungent have been placed on deposit with the American Type Culture Collection (ATCC), 10801 University Blvd., Manassas, Va., 20110-2209 under Deposit Accession Number on.

This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. These *Capsicum annuum* seeds will be replenished should it become non-viable at the depository.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A method of producing *Capsicum annuum* seed, the method comprising the step of:
   crossing a first *Capsicum annuum* plant with a second *Capsicum annuum* plant and harvesting the resultant *Capsicum annuum* seed, wherein said first or second *Capsicum annuum* plant is selected from the group consisting of 96P610, 97P1938, 96P611 and PA47, a representative sample of which has been deposited under ATCC Accession No. 203779, PTA-5749, PTA-5689 and PTA-8808, respectively.

2. The method of claim 1 further comprising the step of planting the resultant *Capsicum annuum* seed and selecting a *Capsicum annuum* plant having a height equal to or less than 29.0 cm or upright fruit wherein said fruit has a fruit weight of less than 5 grams per fruit and further wherein said fruit, when immature, is a color other than green.

3. The method of claim 2 further comprising the step of collecting the seed of the selected plant.

4. A method of producing a *Capsicum annuum* plant in a pepper breeding program, the method comprising the steps of:
   a. obtaining a *Capsicum annuum* plant selected from the group consisting of 96P610, 97P1938, 96P611 and PA47, a representative sample of which has been deposited under ATCC Accession No. 203779, PTA-5749, PTA-5689 and PTA-8808, respectively; and
   b. using the *Capsicum annuum* plant obtained in step a) as a parent in a plant breeding program.

5. The method of claim 4 further comprising the step of selecting a *Capsicum annuum* plant having a height equal to or less than 29.0 cm or upright fruit, wherein said fruit has a fruit weight of less than 5 grams per fruit and further wherein said fruit, when immature, is a color other than green.

6. The method of claim 5 further comprising the step of collecting the seed of the selected plant.

7. The seed produced by the method of claim 1.

8. The plant produced by the method of claim 2.

9. The plant produced by the method of claim 4.

10. The plant produced by the method of claim 5.

* * * * *

UNITED STATES PATENT AND TRADEMARK OFFICE
CERTIFICATE OF CORRECTION

| | | |
|---|---|---|
| PATENT NO. | : 7,393,995 B2 | Page 1 of 1 |
| APPLICATION NO. | : 11/247632 | |
| DATED | : July 1, 2008 | |
| INVENTOR(S) | : Marlin Edwards | |

It is certified that error appears in the above-identified patent and that said Letters Patent is hereby corrected as shown below:

Column 21, line 61, remove "PA47" and replace with -- 96P610 --; line 65, remove "PTA-8808 on Dec. 5, 2007" and replace with -- 203779 on Feb. 17, 1999 --.

Column 22, line 40, remove "on." and replace with -- PTA-8808 on Dec. 5, 2007 --; lines 41-48 should be included as part of the previous paragraph, with lines 35-40, and not as the beginning of a new paragraph.

Signed and Sealed this

Twenty-fourth Day of March, 2009

JOHN DOLL
*Acting Director of the United States Patent and Trademark Office*